United States Patent
Christian et al.

(10) Patent No.: US 8,172,830 B2
(45) Date of Patent: *May 8, 2012

(54) COMPOSITE OPHTHALMIC MICROCANNULA

(75) Inventors: Jeffrey J. Christian, Morgan Hill, CA (US); Stanley R. Conston, San Carlos, CA (US); David J. Kupiecki, San Francisco, CA (US); John McKenzie, San Carlos, CA (US)

(73) Assignee: Iscience Interventional Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/729,603

(22) Filed: Mar. 28, 2007

(65) Prior Publication Data

US 2007/0179471 A1 Aug. 2, 2007

Related U.S. Application Data

(63) Continuation of application No. 11/042,825, filed on Jan. 24, 2005, now Pat. No. 7,207,980.

(60) Provisional application No. 60/538,625, filed on Jan. 23, 2004.

(51) Int. Cl.
*A61M 25/00* (2006.01)

(52) U.S. Cl. ......... 604/524; 604/523; 604/525; 604/526

(58) Field of Classification Search .................. 604/521, 604/523–527
See application file for complete search history.

(56) References Cited

U.S. PATENT DOCUMENTS

| | | | | |
|---|---|---|---|---|
| 4,418,688 A | * | 12/1983 | Loeb | 600/108 |
| 4,607,622 A | * | 8/1986 | Fritch et al. | 600/108 |
| 5,209,734 A | * | 5/1993 | Hurley et al. | 604/158 |
| 5,308,342 A | | 5/1994 | Sepetka et al. | |
| 5,360,425 A | | 11/1994 | Cho | |
| 5,431,646 A | * | 7/1995 | Vassiliadis et al. | 606/6 |
| 5,486,165 A | | 1/1996 | Stegmann | |
| 5,569,218 A | | 10/1996 | Berg | |
| 5,791,036 A | | 8/1998 | Goodin et al. | |
| 5,911,715 A | | 6/1999 | Berg et al. | |
| 5,964,747 A | * | 10/1999 | Eaton et al. | 606/4 |
| 6,036,670 A | | 3/2000 | Wijeratne et al. | |
| 6,074,361 A | * | 6/2000 | Jacobs | 604/95.01 |
| 6,117,116 A | | 9/2000 | Walsh | |
| 6,142,990 A | * | 11/2000 | Burk | 606/6 |
| 6,183,462 B1 | | 2/2001 | Beals | |
| 6,355,027 B1 | | 3/2002 | Le et al. | |
| 6,451,005 B1 | * | 9/2002 | Saitou et al. | 604/526 |
| 6,524,275 B1 | | 2/2003 | Lynch et al. | |
| 6,524,296 B1 | * | 2/2003 | Beals | 604/500 |
| 2001/0011165 A1 | * | 8/2001 | Engelson et al. | 604/265 |
| 2001/0021840 A1 | * | 9/2001 | Suresh et al. | 604/525 |
| 2004/0147950 A1 | | 7/2004 | Mueller, Jr. et al. | |

FOREIGN PATENT DOCUMENTS

CH 691758 10/2001

(Continued)

*Primary Examiner* — Kevin C Sirmons
*Assistant Examiner* — Brandy C Scott
(74) *Attorney, Agent, or Firm* — GSS Law Group; James J. Leary; Carol D. Titus

(57) ABSTRACT

Microcannulae are constructed with multiple components in a composite design, allowing the microcannulae to have varying mechanical and delivery properties that will enable ophthalmic treatments by minimally invasive means. The microcannula includes at least one flexible, tubular communicating element with an outer diameter of 350 microns or less, a proximal connector for introduction of materials, energy or tools. It may also include a reinforcing member attached to the communicating element, which may be designed to create variable stiffness along the length of the microcannula. The microcannula may also include other features such as a signal beacon near the distal tip.

41 Claims, 2 Drawing Sheets

FOREIGN PATENT DOCUMENTS

| | | |
|---|---|---|
| EP | 1114627 A1 | 7/2001 |
| WO | WO 00/64389 A1 | 11/2000 |
| WO | WO 01/37767 A1 | 5/2001 |
| WO | WO 01/41685 A2 | 6/2001 |
| WO | WO 02/074052 A1 | 9/2002 |
| WO | WO 03/045290 A1 | 6/2003 |
| WO | WO 2004/093761 A1 | 11/2004 |

* cited by examiner

COMPOSITE OPHTHALMIC MICROCANNULA

CROSS-REFERENCE TO OTHER APPLICATIONS

This application is a continuation of U.S. utility patent application Ser. No. 11/042,825, filed Jan. 24, 2005 now U.S. Pat. No. 7,207,980, which claims the benefit of U.S. provisional patent application Ser. No. 60/538,625, filed Jan. 23, 2004, the disclosures of which are hereby incorporated by reference in their entirety.

FIELD OF THE INVENTION

The present invention relates to microcannulae that are constructed with multiple components in a composite design. The composite design allows the microcannula to have varying mechanical and delivery properties that will enable ophthalmic treatments by minimally invasive means.

BACKGROUND OF INVENTION

A variety of catheters and cannulae are used in ophthalmic surgery to deliver fluid, gas, suction and energy to select regions of the eye. Existing cannulae are typically straight or curved segments of rigid plastic or metal tubing attached to a connector. In the development of advanced surgical methods to treat the eye, it is desired to have cannulae that can access and be advanced into very small structures or channels in the eye to perform minimally invasive procedures. Such microcannulae that access curved or tortuous spaces such as Schlemm's Canal or small blood vessels require a combination of flexibility and "pushability", while maintaining a diameter in the range of 50 to 350 microns. The present invention describes microcannulae that are constructed with multiple components in a composite design. The composite design allows the microcannula to have varying mechanical and delivery properties that will enable ophthalmic treatments by minimally invasive means.

PRIOR ART

U.S. Pat. No. 6,524,275
Lynch, et al Feb. 25, 2003
Inflatable device and method for treating glaucoma
U.S. Pat. No. 6,355,027
Le, et al. Mar. 12, 2002
Flexible microcatheter
U.S. Pat. No. 6,142,990
Burk Nov. 7, 2000
Medical apparatus, especially for reducing intraocular pressure
U.S. Pat. No. 6,036,670
Wijeratne, et al. Mar. 14, 2000
Coiled transition balloon catheter, assembly and procedure
U.S. Pat. No. 5,911,715
Berg, et al. Jun. 15, 1999
Guide catheter having selected flexural modulus segments
U.S. Pat. No. 5,791,036
Goodin, et al. Aug. 11, 1998
Catheter transition system
U.S. Pat. No. 5,569,218
Berg Oct. 29, 1996
Elastic guide catheter transition element
U.S. Pat. No. 5,486,165
Stegmann Jan. 23, 1996
Method and appliance for maintaining the natural intraocular pressure
U.S. Pat. No. 5,308,342
Sepetka, et al. May 3, 1994
Variable stiffness catheter
Patent Number: EP1114627 A1
Inventor(s): Grieshaber Hans R (Ch); Stegmann Robert Prof M D (Za)
Method and apparatus to improve the outflow of the aqueous humor of an eye
Patent Number: WO0064389
Inventor(s): Brown Reay H (Us); Lynch Mary G (Us); King Spencer B Iii (Us)
Trabeculotomy device and method for treating glaucoma
Patent Number: WO02074052
Inventor(s): Smedley Gregory T; Gharib Morteza; Tu Hosheng
Applicator and methods for placing a trabecular shunt for glaucoma treatment
Patent Number: WO03/045290
Inventor(s): Conston S, Yamamoto R
Ophthalmic Microsurgical System
Patent Number WO2004/093761
Inventor(s): Conston S, Kupiecki D, McKenzie J, Yamamoto R
Ophthalmic Microsurgical Instruments

SUMMARY OF THE INVENTION

A composite microcannula for access and advancement into a tissue space of the eye comprising at least one flexible, tubular communicating element with an outer diameter of 350 microns or less, with proximal and distal ends, and sized to fit within the tissue space; a proximal connector for introduction of materials, energy and tools; and a reinforcing member in conjunction with the communicating element.

A microcannula having a reinforcing member that provides for greater axial and flexural stiffness at the proximal end of the microcannula and lower axial and flexural stiffness to the distal end.

A microcannula having a reinforcing element formed of metal.

A microcannula having a communicating element formed of a flexible polymer and a reinforcing member formed of metal.

A microcannula having two or more communicating elements.

A microcannula having communicating elements in concentric alignment.

A microcannula having communicating elements in parallel alignment

A microcannula comprising two communicating elements where the second communicating element is located within the lumen of the first communicating element.

A microcannula having two or more reinforcing elements.

A microcannula having a reinforcing element in the form of a coil.

A microcannula having a reinforcing element that is tapered toward the distal end of the microcannula.

A microcannula having a communicating element formed of a segment of tubing, optical fiber or an electrical conductor.

A microcannula designed to fit within a tissue space such as Schlemm's Canal, an aqueous collector channel, aqueous vein, suprachoroidal space or retinal blood vessel of the eye.

A microcannula having a distal tip with a rounded leading edge.

A microcannula having a communicating element and a reinforcing element that are joined by an outer sheath.

A microcannula having an outer sheath formed of heat shrink tubing.

A microcannula having an outer sheath that is thermally fused to the communicating element(s).

A microcannula having a communicating element and a reinforcing element that are joined with an adhesive.

A microcannula having a communicating element and a reinforcing element that are bonded through non-adhesive means such as thermal or ultrasonic welding.

A composite microcannula for access and advancement into a tissue space of the eye comprising at least one flexible, tubular communicating element with an outer diameter of 350 microns or less, with proximal and distal ends, to fit within the tissue space; and a coiled metal reinforcing member attached to the communicating element; wherein the communicating element is formed of a flexible polymer or a superelastic metal alloy.

A composite microcannula for access and advancement into a tissue space of the eye comprising at least one flexible, tubular communicating element with an outer diameter of 350 microns or less, with proximal and distal ends, and a fluid communicating lumen sized to fit within the tissue space; a proximal connector for introduction of fluid and a second communicating element comprising an optical fiber, where the microcannula provides means for the delivery of both fluid and a visible light signal to the distal tip of the microcannula simultaneously.

A composite microcannula for access and advancement into a tissue space of the eye comprising at least one flexible, tubular communicating element with an outer diameter of 350 microns or less, with proximal and distal ends, and a fluid communicating lumen sized to fit within the tissue space; a proximal connector for introduction of fluid and a second communicating element comprising an optical fiber, where the microcannula has a rounded distal tip and provides means for the delivery of both fluid and a visible light signal to the distal tip of the microcannula simultaneously.

A composite microcannula for access and advancement into a tissue space of the eye comprising at least one flexible, tubular communicating element with an outer diameter of 350 microns or less, with proximal and distal ends, and a fluid communicating lumen sized to fit within the tissue space; a proximal connector for introduction of fluid, a second communicating element comprising an optical fiber, and a reinforcing member, where the microcannula provides means for the delivery of both fluid and a visible light signal at the distal tip of the microcannula simultaneously.

DESCRIPTION OF INVENTION

Figure 1:
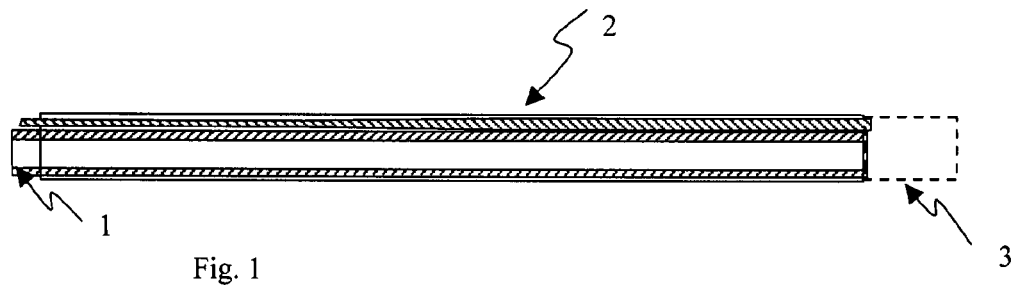
FIG. 1 is a cross-sectional view of a composite microcannula having a tapered reinforcing element.

The invention comprises a microcannula designed to be advanced into very small tissue spaces during surgery. In particular for ophthalmic surgery, the microcannula may be used to cannulate Schlemm's Canal, aqueous humor collector channels, aqueous veins, retinal veins and the suprachoroidal space. Such structures range from 50 to 250 microns in diameter, thereby restricting the outer diameter of the microcannula to similar dimensions. The microcannula comprises a flexible elongated element with a connector at the proximal end 3, a distal tip, and a communicating channel 1 therebetween, as seen in FIG. 1. The communicating channel 1 of the microcannula may be used to deliver fluids, materials, energy, gases, suction, surgical tools and implants to a distal surgical site for a variety of surgical tasks. The communicating channel 1 may be the lumen of a tube-like elongated element to transport materials, an optical fiber to transport light energy, or a wire to transport electrical signals. The flexible elongated element with a communicating channel 1 is referred to as the communicating element. A single communicating element may have more than one communicating channel.

The microcannula of the present invention incorporates specific design features that enable it to be placed into very small tissue spaces. A key feature is the use of a composite microcannula design that has the appropriate combination of axial stiffness and compliance. The microcannula is desired to be flexible to allow it to be advanced along a curved or tortuous tissue space with minimal tissue trauma, but with sufficient axial stiffness or "pushability" to allow transfer of force to advance the microcannula. For a fixed outer dimension, the mechanical properties of the microcannula may be tailored by the selection of materials of construction and cross-sectional dimensions. In one embodiment, a reinforcing element 2 is attached to the outside of a communicating element. Typically, the reinforcing element 2 comprises a material with higher flexural modulus than the communicating element. The communicating element may be a thin wall polymer or metallic tube. The reinforcing element 2 may be formed of any high modulus material such as, but not limited to, metals including stainless steel and nickel titanium alloys, ceramic fibers and high modulus polymers, filled or reinforced polymers, and polymer-polymer composites.

Figure 2:
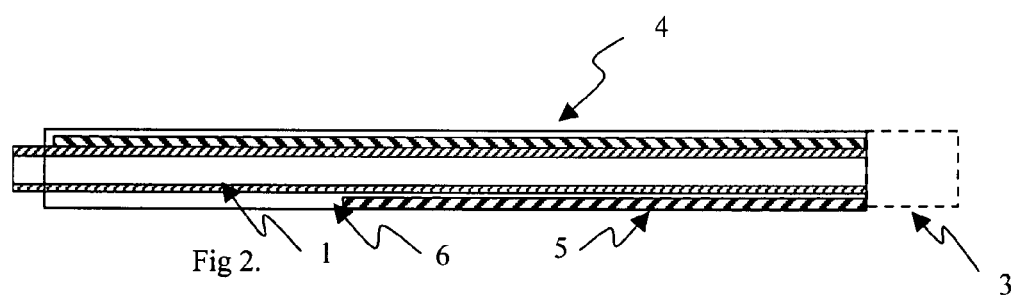
FIG. 2 is a cross-sectional view of a composite microcannula having two reinforcing elements, one full length and one partial length.

For optimal use in small tissue spaces, the microcannula is desired to be flexible at the distal tip, but transitioning to more rigid mechanical properties toward the proximal end. The transition may comprise one or more steps in mechanical compliance, or a gradient of compliance along the length of the microcannula. The transition in mechanical properties may be accomplished by a change in the cross-sectional area or material properties of the microcannula along its length, the incorporation of one or more stiffening members, or a combination thereof. In one embodiment of the invention, the microcannula incorporates a communicating element 1 forming the communicating channel 1 fabricated from a flexible polymer with two reinforcing members 4, 5 attached along the length, as seen in FIG. 2. One of the reinforcing members 5 extends along the communicating element but not completely to the distal tip, while the other reinforcing member 4 extends completely to the distal tip to provide a transition in flexural compliance. The reinforcing members 4, 5 may be formed of a high modulus polymer or metal. In a similar embodiment, a single reinforcing member with a transition in flexural stiffness, such as a tapered wire 2, may be used to reinforce the communicating element. Alternatively, a reinforcing member may be formed of sequential segments of varying modulus or cross-sectional dimensions. The reinforcing elements may be held in place by an outer sheath 6 which may comprise a tight fitting polymer tube or polymer shrink tubing. Alternatively, the reinforcing elements may be adhered or bonded to the communicating element, or may be fully or partially contained within the communicating element.

The reinforcing element may also provide kink resistance to the communicating element. This is especially advantageous for use with communicating elements fabricated from high modulus polymers, such as polyimide, polysulfone, ultra-high molecular weight polyethylene and fiber reinforced polymer composites, which kink or deform under high loads, forming a permanent mechanical defect. The reinforcing element may also comprise a malleable material to allow the shape of the microcannula to be adjusted manually to better accommodate a curved shape of the tissue space. Possible malleable materials for the reinforcing element include but are not limited to steel, silver and platinum alloys.

Figure 3:
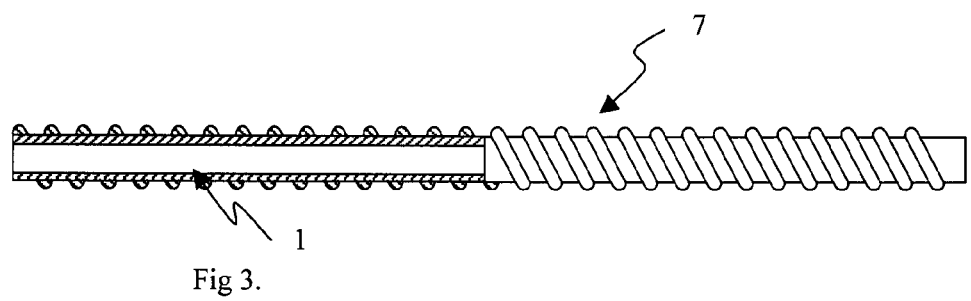
FIG. 3 is a part cross-sectional view of a composite microcannula having a spiral wound reinforcing element in the form of a round wire.
Figure 4:
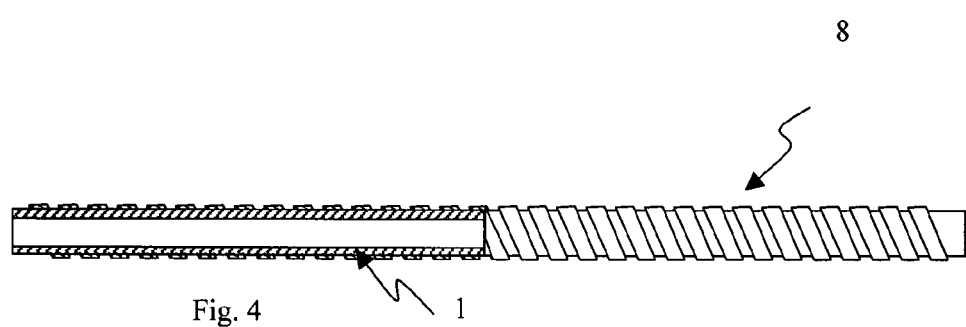
FIG. 4 is a part cross-sectional view of a composite microcannula having a spiral wound reinforcing element in the form of a flat ribbon.

The reinforcement of the communicating element may also be accomplished by the incorporation of coil-like members to provide high flexural compliance but also high axial stiffness for pushability, as seen in FIGS. 3 & 4. A reinforcing member 7, 8 attached to an outer sheath may be a coiled or wound element on or formed into the exterior surface of the sheath. The reinforcing member 7, 8 may be any suitable high modulus material including metals such as, but not limited to, stainless steel, titanium and superelastic alloys, ceramics such as ceramic fibers, and high modulus polymers or composite polymer structures such as carbon fiber reinforced epoxy. The members may have any suitable cross-section such as round or semi-circular 7 or rectangular 8, as in the case of a flat wire winding. The winding pitch of the reinforcing members may be constant, or it may be varied to achieve differential flexural properties along the length of the microcannula. Multiple wound elements may be incorporated, with the elements being formed of like or different materials. The reinforcing element or multiple reinforcing elements may also be configured to provide a preferred deflection orientation of the microcannula.

The composite microcannula of the present invention may also include multiple communicating elements. In one embodiment, the microcannula may include two or more elongated communicating elements with a reinforcing member to form a composite structure. The components may be adhered together, placed within an outer sheath, such as heat shrink tubing or an outer communicating element may contain one or more other communicating elements. One of the communicating elements may be used for transport of materials, another for transport of light or energy, thus providing a multifunctional surgical tool. The communicating elements may be aligned side-by-side or arranged around one or more reinforcing elements. In one embodiment, one communicating element with an annular cross-section forming a lumen may be fitted with a second communicating element within the lumen. Such concentric alignment of communicating elements may also be used in combination with other communicating elements that are not in concentric alignment.

In one particular embodiment, the composite microcannula may be used only to transfer mechanical energy. For example, the microcannula may be used to advance into a tissue space and used to snare a foreign object or area of tissue. In such cases, the elongated communicating element may be a material such as a wire, polymer, or fiber composite of appropriate mechanical properties. An inner member, which fits and slides within the communicating element, may also be incorporated, the inner member having at least a proximal end and a distal tip. Advancement or withdrawal of the inner member may be used to change the shape of the distal tip of the microcannula, or alternatively to effect a mechanical action at the distal tip.

In one embodiment, the microcannula also comprises a proximal connector for the communicating element. The connector may serve to connect a supply of material or energy, such as an infusion syringe or light source to the communicating channel 1 of the communicating element. Additionally, the microcannula may contain a central section comprising a single or multiple side connectors to allow the attachment of ancillary equipment such as syringes, vacuum or pressure sources, sensing means and the like. The attachment connectors may use standard designs such as Luer fittings or may be designed to only accept connection with specific components. In another embodiment, the composite microcannula may incorporate fenestrations or windows along the length. The fenestrations may be used to deliver materials from the sides of the microcannula, for instance the delivery of therapeutic agents to the tissues of Schlemm's Canal. Alternately, with the connection of a vacuum generating device to the proximal connector of the communicating element, the fenestrations may be used to provide suction against soft tissues. The suction may be used for the removal of tissue or may be used to anchor the microcannula in place while another element is advanced through the microcannula. For example, a composite suction microcannula may be used to strip the juxtacanicular tissues from the inner wall of Schlemm's Canal.

The communicating element may be formed of a thin walled polymer or metallic tube of sufficient stiffness to allow it to be advanced into tissues or along a tissue space such as Schlemm's Canal, and of sufficient flexibility to follow the circular tract of Schlemm's Canal. Due to the small size of the target tissue spaces, the microcannula must be appropriately sized. Typically, the microcannula is sized in the range of 50 to 350 microns outer diameter with a wall thickness from 10-100 microns. The cross-section of the microcannula may be round or oval or other bound shape to approximate the shape of a tissue space such as Schlemm's Canal. In some embodiments, a predetermined curvature may be applied to the device during fabrication.

Suitable materials for the communicating element include metals, polyetheretherketone (PEEK), polyethylene, polypropylene, polyimide, polyamide, polysulfone, polyether block amide (PEBAX), fluoropolymers or similar materials. The outer sheath may also have surface treatments such as lubricious coatings to assist in tissue penetration and ultrasound or light interactive coatings to aid in location and guidance. The microcannula may also have markings on the exterior for assessment of depth in the tissue space. For example, the markings may take the form of rings around the outer shaft located at regular intervals along the length of the microcannula. The external markings allow user assessment of the length of the tissue space or channel accessed by the microcannula, and the approximate location of the microcannula tip.

Figure 5:
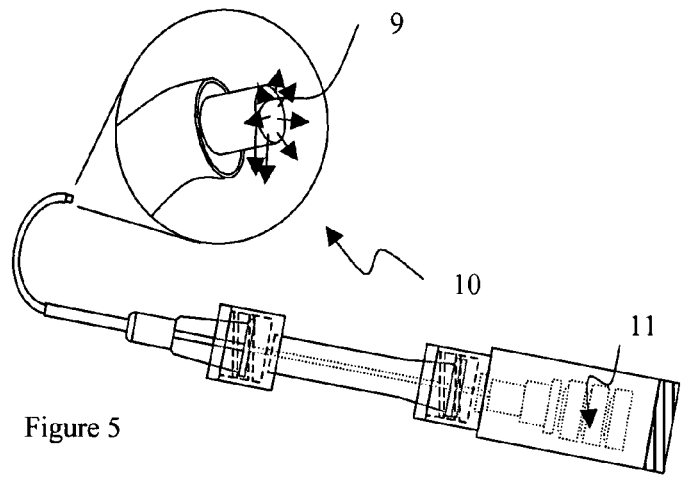
FIG. 5 is a side view and close up view of a curved composite microcannula having a signaling beacon tip extending beyond the distal tip of outer sheath.

In an embodiment of the invention, a first communicating element used for initial placement of the microcannula has a signaling beacon to identify the location of the microcannula distal tip relative to the target tissues, as seen in FIG. 5. The signaling means may comprise an echogenic material for ultrasound guidance, an optically active material for optical guidance or a light source for visual guidance placed at the microcannula tip or placed to indicate the position of the microcannula tip. In one embodiment, a plastic optical fiber (POF) 9 is used as a communicating element to provide a bright visual light source at the distal tip 10. The distal tip 10 of the POF 9 is positioned proximal to, near or slightly beyond the distal end of the microcannula sheath and the emitted signal may be detected through tissues visually or using sensing means such as infrared imaging. The POF 9 may also have a tip that is beveled, mirrored or otherwise configured to provide for a directional beacon. The beacon may be illuminated by a laser, laser diode, light-emitting diode, or an incandescent source such as a mercury halogen lamp. In an alternate embodiment, the signaling means may comprise visualization aids along the length of the microcannula, for example a side emitting optical fiber of discrete length leading up to the distal end or at a known point along the microcannula may be used to indicate the position of the microcannula and the distal tip. Upon placement of the microcannula at the target tissues, the beacon assembly 11 and POF 9 may be removed. The connection point may be sealed with a cap or with a self-sealing mechanism such as a one-way valve or an elastomer seal. Alternatively, the POF may be placed co-linear to or within the lumen of a delivery communicating channel, allowing for delivery of fluids or gases through the delivery communicating channel without requiring removal of the beacon assembly.

Alternate embodiments of the microcannula may use other imaging technologies to locate the signal beacon. Other possible imaging technologies include but are not limited to magnetic resonance imaging, fluoroscopy and ultrasound. In these embodiments, the beacon signal may take other forms to match the imaging technology such as a radiopaque marker attached to or embedded at or near the distal tip of the microcannula. Alternatively or in addition, an echogenic material or coating may be added to the distal tip, etc.

Figure 6:
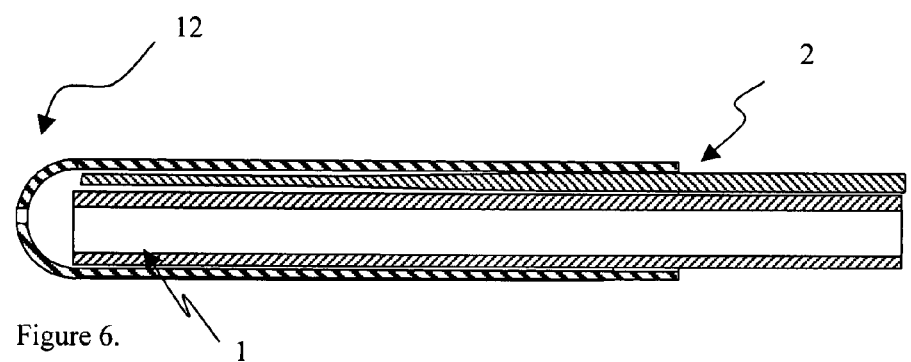
FIG. 6 is a cross-sectional view of a composite microcannula having a tapered reinforcing element and a rounded distal tip.
Figure 7:
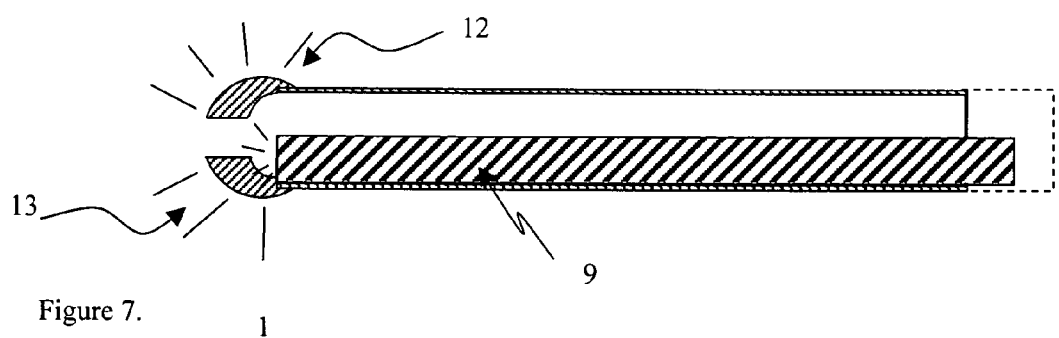
FIG. 7 is a cross-sectional view of a composite microcannula having a ball-end distal tip formed separately from the communicating element and an optical fiber to provide for a beacon with light dispersed at the tip.

It is also preferred for the microcannula to have a rounded distal tip 12 to minimize tissue trauma and aid the ability of the microcannula to be advanced into small tissue spaces, as seen in FIGS. 6 and 7. The rounded tip 12 may be the same outer diameter as the microcannula or larger, depending on the specific properties desired. The rounded tip 12 may be formed and attached to the microcannula during assembly or alternatively, the microcannula tip may be processed by a secondary operation to form a rounded contour. When the rounded tip 12 is used in conjunction with a light emitting signaling beacon 9 such that the light is delivered proximal to the rounded tip, the tip acts to disperse the light 13. The dispersed light aids visualization when viewing the microcannula off axis, for example when advancing the microcannula in Schlemm's Canal.

Another key feature of the invention is the use of a communicating element to deliver fluid to the distal tip during advancement of the microcannula within the tissue space. The injection of small amounts of fluid may serve to open the tissue space ahead of the microcannula tip and lubricate the channel to greatly increase the ability to advance the microcannula atraumatically. Delivery of surgical viscoelastic materials such as hyaluronic acid solutions and gels are especially efficacious in aiding advancement and placement of the microcannula. Delivery of fluids, especially gel-like viscoelastic materials, allows for the dilation of the tissue space in the circumstance that a constriction or partial blockage is reached during advancement of the microcannula. A particularly effective embodiment comprises a microcannula with a communicating element such as an optical fiber to provide a signaling beacon at the microcannula tip and a second communicating element to deliver a fluid such as a solution of hyaluronic acid to the microcannula tip while the signaling beacon is active. Such a microcannula may be manually manipulated and used to deliver fluids to aid microcannula advancement while simultaneously observing the microcannula tip location along the tissue space. The combination of fluid delivery in the path of the microcannula and the observation of the microcannula tip when advanced, retracted and torsioned allows precisely controlled manipulation and advancement in tight tissue spaces. The ease of manipulation is further aided with the addition of a reinforcing member to the communicating element of the microcannula.

EXAMPLES

Example 1

In the following example, a composite microcannula with two communicating elements was fabricated. A communicating element with a lumen (Polyimide Tubing 0.003 inch ID×0.004 inch OD), a second communicating element comprising a plastic optical fiber (85-100 microns, 0.0034-0.0039 inch OD), a reinforcement element (304SS wire ground to 0.001 inches in the distal 2.5 inches tapering up over a 1.0 inch length to a diameter of 0.003 inches for the remaining length of the microcannula), and an outer sheath comprising polyethylene teraphthalate (PET) shrink tubing (0.008 inch ID and 0.00025 inch wall thickness), were all cut to lengths appropriate for setting the final overall length of the microcannula. The distal ends of the inner components were then aligned flush and joined with an adhesive. The reinforcing element was tapered and aligned to provide more flexibility distally and stiffer reinforcement more proximal in the microcannula. The three elements were aligned in a triangular pattern rather than an in-line pattern to create an assembled profile with the smallest major-axis dimension. The assembly of multiple components was then inserted into the heat shrink tubing outer sheath so that the inner elements were aligned for capture in the heat shrink tubing. At the proximal end of the microcannula assembly, the two communicating elements were extended outside of the heat shrink tubing and separated.

The assembly was placed in a hot air stream at 220-240 degrees F., so the heat shrink recovered and the inner elements were captured to form a multi-component shaft of the microcannula. The composite microcannula demonstrated a final outer dimension of 200 to 230 microns with a lumen of 75 microns. To finish the assembly, extension communicating elements were bonded to the proximal end of the two communicating elements respectively. The extensions were finished by adding a Luer infusion connector and an optical connector to serve as interfaces to the communicating elements. Testing of the completed microcannula was performed, demonstrating simultaneous fluid delivery from the Luer connector and light delivery from the optical connector to the microcannula tip.

Example 2

The microcannula fabricated in Example 1 was tested in accessing Schlemm's Canal of an enucleated human eye. The first communicating element, the infusion lumen, was attached to a syringe filled with fluid at the proximal Luer connection. The second communicating element, the optical fiber, was attached to a light emitting source at the proximal connection. Operating at the temporal-superior segment of the anterior portion of the eye, two radial incisions were made to a depth of Schlemm's Canal and extending from the clear cornea approximately 3 mm posterior. A third incision was made across the posterior end of the radial incisions to define a surgical flap. The flap was then excised up toward the limbus, exposing Schlemm's Canal. The distal tip of the composite microcannula was inserted into Schlemm's Canal. The light source for the second communicating element was activated and the microcannula was advanced along Schlemm's Canal. The light emitting from the microcannula tip was seen through the sclera and used to help guide the microcannula. The microcannula was advanced along Schlemm's Canal until the tip was seen reaching an appropriate location. The syringe connected to the first communicating element extension was used to inject fluid (Healon GV, Advanced Medical Optics, Inc.) into Schlemm's Canal as needed to aid microcannula advancement. After the desired microcannula positioning was completed, the microcannula was repositioned for additional fluid injections and subsequently completely retracted from Schlemm's Canal.

Example 3

In the following example, an atraumatic rounded distal tip component was fabricated for placement over a composite microcannula. Polyethylene teraphthalate (PET) shrink tubing (Advanced Polymers, Nashua N.H.) 0.008 inch ID and 0.00025 inch wall thickness was obtained. A length of shrink tubing approximately 2 cm long was placed over a mandrel comprised of a section of hypodermic tubing 0.003 inch× 0.007 inch diameter. Teflon coated steel wire, 0.0025 inch diameter was held inside the hypodermic tubing and extending beyond the end of the shrink tubing. Under stereomicroscope visualization, a point heat source (adjustable soldering iron) set to 500 degrees C. was brought into close proximity to the end of the heat shrink tubing. The heat was allowed to melt the end of the tube without touching the heat source to the polymer. The surface tension of the polymer melt created a rounded "ball-end" tip with a 0.0025 inch diameter lumen. The polymer was allowed to cool and then stripped off of the mandrel and wire. The length of PET shrink tubing held beyond the end of the mandrel determined the final diameter of the rounded tip. Approximately 0.08 inches of extension yielded tips approximately 0.008 inch or 200 micron outer diameter.

The finished component was then drawn over the distal end of a composite microcannula similar to Example 1, which was 0.0075 inches or 190 microns in largest diameter. The tip component was butted up to the end of the composite elements and then shrunk in place with a hot air stream at 240 degrees F. to attach the tip.

Example 4

In the following example, the body of a composite microcannula was formed out of a wire coil and polymer heat shrink tubing. The coil was fabricated by progressively winding a 0.003 inch by 0.001 inch stainless steel ribbon under 20 grams tension around a 0.0055 inch diameter stainless steel mandrel. Following removal from the mandrel, the resulting wire ribbon coil had an outside diameter of 0.008 inches or 200 microns, an inside diameter of 0.006 inches or 150 microns, and overall length of approximately 5 inches. A 6 inches long piece of 0.010 inch or 250 micron ID PET heat shrink with a preformed rounded tip at one end was slipped over the coil and recovered using hot air over the entire length of the coil.

A 0.004 inch diameter optical fiber was then loaded into the lumen of the microcannula and advanced to the distal end. The proximal ends were terminated into a fluid infusion lumen and 0.5 mm diameter optical fiber respectively. The distal portion of the assembly was found to have desirable mechanical characteristics of flexibility and resistance to kinking.

Example 5

An experiment was performed to test the coil-wound microcannula design as described in Example 3. Whole globe human eyes were obtained from a tissue bank. The enucleated eyes were prepared by first injecting the vitreous chamber with phosphate buffered saline to replace fluid lost postmortem and bring the globes to a natural tone. Operating at the temporal-superior segment of the anterior portion of the eye, two radial incisions were made to a depth of Schlemm's Canal and extending from the clear cornea approximately 3 mm posterior. A third incision was made across the posterior end of the radial incisions to define a surgical flap. The flap was then excised up toward the limbus, exposing Schlemm's Canal. The microcannula was inserted into Schlemm's Canal and advanced to approximately 90 degrees around from the access site. The metal coil was able to be seen through the scleral wall allowing the amount of microcannula advancement to be determined.

Example 6

In the following example, a composite microcannula with several communicating elements in parallel alignment forming a distal segment with a maximum outer diameter of 250 microns was fabricated. The outer member comprised a tubular structure and the two internal communicating elements comprised elongated linear elements. At the distal end of the outer structure, an atraumatic spherical-shaped distal tip was formed. A communicating lumen was formed in the annular space between the outer tube and the inner members. The inner members comprised an optical fiber and a reinforcement element. The outer member was a tubular structure comprised of three sizes of PEBAX (polyamide/polyether copolymer), 63 durometer tubing:
1) Proximal Section 0.016 inch ID×0.026 inch OD, 24 inch length
2) Mid Section 0.010 inch ID×0.014 inch OD, 4 inch length
3) Distal Section 0.006 inch ID×0.008 inch OD, 1.8 inch length The outer tubular element was constructed by first cutting the individual shaft segments to lengths appropriate for setting the final overall length of the microcannula. The mid section was inserted into the proximal section with appropriate length for an overlapping bond. The tubular elements were then bonded together with an adhesive or by melt-fusing the polymeric tubes together with a controlled heat process. The distal section was bonded to the mid shaft similarly. These tubes were bonded together to form a decreasing outer diameter toward the distal tip.

The reinforcement element comprised 304 Stainless Steel wire size 0.0010+/−0.0005 inch OD, and the optical fiber comprised a plastic optical fiber fabricated from polystyrene and polymethylmethacrylate with an 85 to 100 micron OD. The reinforcement element and the optical fiber were cut to lengths appropriate for setting the final overall length of the microcannula. The reinforcement element and optical fiber were inserted into the outer member assembly. The inner elements were aligned with the distal tip of the distal shaft.

An atraumatic rounded tip was formed at the end of the distal section. A quick drying UV curable adhesive (Loctite Brand 4305) was applied to the outer section of the distal tip. An adhesive of medium to high viscosity was chosen so that the adhesive application formed a bulbous structure approximately 0.001 inch thickness. A small, approximately 0.03 microliter amount of adhesive was used to create the tip. The adhesive was cured to form the spherically shaped atraumatic tip with a diameter of 0.010 inches or 250 microns.

The free end of the infusion lumen was terminated with a female Luer port. The proximal end of the optical fiber was connected to a Plastic Optical Fiber (POF) that terminated in an optical SMA connector.

The area of the microcannula assembly where the optical fiber and reinforcement enter the inside of the outer member was sheathed in a protective plastic housing forming a hub. The hub also provided a means for manipulation of the microcannula.

The optical SMA termination was connected to a light source and light was conducted to the tip of the microcannula to provide a signal beacon. The Luer termination was connected to a fluid-filled syringe and activation of the syringe resulted in fluid delivery through the microcannula exiting from the distal tip. Delivery of the signal beacon light and fluid could be activated individually or simultaneously.

Example 7

In the following example, a composite microcannula with several communicating elements in parallel alignment forming a distal segment with a maximum outer diameter of 350 microns was fabricated similarly to Example 6. In this embodiment the outer member was constructed with three sizes of PEBAX tubing with slightly larger dimensions:
1) Proximal Section 0.016 inch ID×0.026 inch OD, 24 inch length
2) Mid Section 0.0130 inch ID×0.015 inch OD, 4 inch length
3) Distal Section 0.008 inch ID×0.012 inch OD, 1.8 inch length A spherically shaped atraumatic tip was fabricated on the microcannula by the method described in Example 6, forming a distal tip with a diameter of 0.014 inches or 350 microns. In this embodiment, no reinforcing element was placed into this cannula construction, however a plastic optical fiber was incorporated similar to Example 6.

The optical SMA termination was connected to a light source and light was conducted to the tip of the microcannula. The Luer termination was connected to a fluid-filled syringe and activation of the syringe resulted in fluid delivery through the microcannula exiting from the distal tip.

Example 8

The composite microcannulae of Example 6 and Example 7 were tested in human eyes similarly to the method of Example 2. The distal tip and distal segments of the microcannulae could be advanced along the entire circumference of Schlemm's Canal for 360 degrees while observing the beacon signal at the microcannula tip through the sclera. Injection of small amounts of hyaluronic acid-based surgical viscoelastic fluid (Healon GV, Advanced Medical Optics Inc.) delivered during advancement of the microcannulae decreased the force required for advancement and provided for more progressive advancement.

Example 9

A composite microcannula with several collinear elements was fabricated similar to Example 6. In this embodiment, the outer structure had no mid section in that the proximal section was connected directly to the distal section.

Example 10

In order to determine the optimal flexural properties of a composite microcannula for introduction into small tissue spaces, a family of microcannulae were fabricated with the same outer dimensions and material characteristics but with varying flexural rigidity. Flexural rigidity of a body is equal to the product of the flexural modulus, E, and the moment of inertia of the cross-section, I, and is typically called EI. The outer sheath comprised PEBAX tubing with 0.008 inch (200 micron) OD and 0.006 inch (150 micron) ID. The sample set comprised the tubing alone without reinforcing element(s), the tubing with a 100 micron outer diameter plastic optical fiber placed within the lumen and the tubing with stainless steel reinforcing wires of varying size in the lumen. The ends of the components were secured with adhesive, while forming an atraumatic spherically shaped tip, as described in Example 6. The lumen allowed fluid delivery to the tip of the microcannula from a proximally attached Luer connector.

The flexural rigidity of the microcannulae were evaluated by mechanical testing. The microcannulae cantilever force-displacement characteristics were tested on a mechanical testing apparatus with a high sensitivity load cell (Instron model 5542, 5N Load Cell). The linear region of the resultant data was used to calculate the measured flexural rigidity of the test samples.

| Microcannula Description | Measured Flexural Rigidity (EI) [kN*m$^2$] |
|---|---|
| PEBAX Outer Sheath | 3.09E−11 |
| PEBAX Outer Sheath with 0.001 in diameter SS wire | 3.76E−11 |
| PEBAX Outer Sheath with 100 micron diameter plastic optical fiber | 6.33E−11 |
| PEBAX Outer Sheath with 0.002 in diameter SS wire | 9.69E−11 |
| PEBAX Outer Sheath with 0.003 in diameter SS wire | 2.86E−10 |
| PEBAX Outer Sheath with 0.004 in diameter SS wire | 7.5E−10 |

Example 11

The microcannulae fabricated in Example 10 were tested for the ability to access Schlemm's Canal of a human eye similar to the methods described in Example 2. In a first trial, the distal tip of the microcannulae were inserted into the Canal and advanced without delivery of fluid from the microcannula tip. The number of degrees of advancement around the eye was recorded for each microcannula. In the next trial, the test was repeated with the delivery of a small amount of viscoelastic fluid (Healon GV, Advanced Medical Optics Inc.) from the microcannula tip during advancement. One property of Healon GV, a hyaluronic acid based viscoelastic fluid, is very high lubricity. Three eyes were used for the evaluation, with cannulations performed both clockwise and counterclockwise from the surgical access site.

When tested for the degree of advancement within Schlemm's Canal, the microcannulae with low flexural rigidity could be slowly advanced along Canal until further advancement was no longer possible due to lack of force transfer. These lower flexural rigidity devices tended to bend or kink when reaching the limit of travel. The microcannulae with very high flexural rigidity could be advanced a short distance until further advancement was no longer possible due to the inability of the microcannula to bend with the curve of Schlemm's Canal. If advanced further, the microcannula with very high flexural rigidity in some cases punctured through the outer wall of the Canal, an undesirable result. The testing was performed by advancing each device manually, attempting to use a comparable maximum force for each test run, so as to maintain an adequate comparison. In cases where the cannula did not traverse the full extent of the Canal, the force required to advance the cannula increased with increased extent of cannulation, which was attributed to interaction of the compliance properties of the device and the frictional forces between the device and the tissues of the Canal.

| Microcannula Flexural Rigidity (EI) [kN*m$^2$] | Degrees Cannulation Achieved - No Fluid Delivery AVG | Degrees Cannulation Achieved - No Fluid Delivery Std Dev | Degrees Cannulation Achieved - Fluid Delivery AVG | Degrees Cannulation Achieved - Fluid Delivery Std Dev |
|---|---|---|---|---|
| 3.09E−11 | 183 | 64 | 360 | 0 |
| 3.76E−11 | 242 | 35 | 360 | 0 |
| 6.33E−11 | 265 | 78 | 360 | 0 |
| 9.69E−11 | 203 | 23 | 360 | 0 |
| 2.86E−10 | 177 | 25 | 360 | 0 |
| 7.5E−10 | 80 | 20 | 89 | 26 |

The results of advancing the microcannulae into Schlemm's Canal without fluid delivery demonstrated an optimal flexural rigidity of approximately 6.33 E−11 kN*m$^2$. Flexural rigidity in the range of 3.09 E−11 to 2.86 E−10 provided a microcannula that was able to access approximately 180 degrees of the eye. Such properties would allow the entire eye to be accessed from a single surgical site by advancing the microcannula in both directions.

The results of advancing the microcannula into Schlemm's Canal with fluid delivery demonstrated improved performance except for the microcannula with the highest flexural rigidity. Flexural rigidity in the range of 3.09 E−11 to 2.86 E−10 kN*m$^2$ coupled with the delivery of a lubricious material (Healon GV) allowed the entire circumference of Schlemm's Canal (360 degrees) to be accessed by the test microcannulae. It was noted that the amount of force required to advance each device was significantly decreased by the presence of the lubricious fluid being delivered from the distal tip of the microcannula during the cannulation. In addition, a number of attempts to advance a microcannula into Schlemm's Canal without fluid delivery were made by depositing a small amount of the viscoelastic fluid at the surgical site and then passing the cannula through the gel. These did not result in any significant decrease in force or increase in advancement of the test devices, indicating the advantage of delivering fluid at the microcannula tip during manipulation and advancement.

Many features have been listed with particular configurations, options, and embodiments. Any one or more of the features described may be added to or combined with any of the other embodiments or other standard devices to create alternate combinations and embodiments.

The preferred embodiments described herein are illustrative only, and although the examples given include many specifics, they are illustrative of only a few possible embodiments of the invention. Other embodiments and modifications will no doubt occur to those skilled in the art. The examples given should only be interpreted as illustrations of some of the preferred embodiments of the invention.

What is claimed is:

1. A composite microcannula for access and advancement into a tissue space of the eye comprising:
   at least one flexible, tubular communicating element configured to fit within the tissue space and having a proximal end and a distal end;
   a proximal connector attached to said proximal end, said proximal connector configured for introduction of materials, energy or tools;
   wherein an outer diameter of said composite microcannula is no more than 350 microns;
   wherein the distal end has a rounded distal tip;
   and an optical fiber capable of delivering light to the rounded tip and wherein, when light is delivered to said rounded tip, said rounded tip acts to disperse the light for improved off-axis visualization.

2. A composite microcannula for access and advancement into a tissue space of the eye comprising:
   a flexible, tubular communicating element configured to fit within the tissue space, the communicating element having a proximal end and a distal end;
   a proximal connector attached to said proximal end, said proximal connector configured for introduction of materials, energy or tools;
   a second communicating element comprising an optical fiber;
   and a rounded distal tip forming the distal end of the microcannula,
   wherein the microcannula is configured such that light is delivered through the optical fiber proximal to the rounded distal tip such that the rounded distal tip disperses the light to improve off-axis visualization and identification of the tip location within a tissue space of the eye.

3. The microcannula of claim 2, wherein the microcannula additionally comprises a reinforcing member connected with the communicating element.

4. The microcannula of claim 2, wherein the microcannula has an outer diameter of not more than 350 microns.

5. The microcannula of claim 2, wherein the composite microcannula has a proximal portion with a flexural rigidity greater than the flexural rigidity of the distal portion.

6. The microcannula of claim 2, wherein the composite microcannula has a flexural rigidity of approximately 3.09 E−11 kN*m$^2$ on a distal portion of the composite microcannula positioned adjacent to the distal end.

7. The microcannula of claim 2, wherein the composite microcannula has a flexural rigidity of approximately 3.76 E−11 kN*m$^2$ on a distal portion of the composite microcannula positioned adjacent to the distal end.

8. The microcannula of claim 2, wherein the composite microcannula has a flexural rigidity of approximately 6.33 E−11 kN*m$^2$ on a distal portion of the composite microcannula positioned adjacent to the distal end.

9. The microcannula of claim 2, wherein the composite microcannula has a flexural rigidity of approximately 9.69 E−11 kN*m$^2$ on a distal portion of the composite microcannula positioned adjacent to the distal end.

10. The microcannula of claim 2, wherein the composite microcannula has a flexural rigidity of approximately 2.86 E−10 kN*m² on a distal portion of the composite microcannula positioned adjacent to the distal end.

11. The microcannula of claim 2, wherein the composite microcannula has a flexural rigidity of 3.09 E−11 to 9.69 E−11 kN*m² on a distal portion of the composite microcannula positioned adjacent to the distal end.

12. The microcannula of claim 2, wherein the composite microcannula has a flexural rigidity of 3.09 E−11 to 6.33 E−11 kN*m² on a distal portion of the composite microcannula positioned adjacent to the distal end.

13. The microcannula of claim 2, wherein the composite microcannula has a flexural rigidity of 3.09 E−11 to 3.76 E−11 kN*m² on a distal portion of the composite microcannula positioned adjacent to the distal end.

14. The microcannula of claim 2, wherein the composite microcannula has a flexural rigidity of 3.76 E−11 kN*m² to 9.69 E−11 kN*m² on a distal portion of the composite microcannula positioned adjacent to the distal end.

15. The microcannula of claim 2, wherein the rounded distal tip of the microcannula is approximately spherical.

16. The microcannula of claim 2, wherein the composite microcannula has a flexural rigidity in the range of 3.09 E−11 to 2.86 E−10 kN*m² on a distal portion of the composite microcannula positioned adjacent to the distal end.

17. A composite microcannula for access and advancement into a tissue space of the eye comprising:
at least one flexible, tubular communicating element having a proximal end, a distal end, and a fluid communicating lumen,
a proximal connector configured for delivery of fluid,
a signal beacon,
and a second communicating element configured to deliver the signal beacon, the signal beacon being capable of emitting light sideways from a distal point on the tubular communicating element for identifying the microcannula distal tip,
wherein an outer diameter of said composite microcannula is no more than 350 microns, and wherein the composite microcannula additionally comprises a rounded distal tip.

18. The microcannula of claim 17, further comprising:
a reinforcing member connected with the tubular communicating element.

19. The microcannula of claim 18, wherein the composite microcannula has a flexural rigidity in the range of 3.09 E−11 to 2.86 E−10 kN*m² on a distal portion of the composite microcannula positioned adjacent to the distal end.

20. The microcannula of claim 18, wherein the reinforcing member provides greater axial and flexural stiffness at the proximal end of the microcannula as compared to the distal end of the microcannula.

21. The microcannula of claim 18, wherein the reinforcing element is malleable to allow manual shaping of the microcannula.

22. The microcannula of claim 18, wherein the reinforcing element comprises a metal.

23. The microcannula of claim 18, wherein the tubular communicating element comprises a flexible polymer and the reinforcing member comprises a metal.

24. The microcannula of claim 18, wherein the signal beacon is configured to emit light sideways from the distal tip of the tubular communicating element.

25. The microcannula of claim 18, wherein the microcannula further comprises at least one additional communicating element.

26. The microcannula of claim 25, wherein the additional communicating element is located within a lumen of the first communicating element.

27. The microcannula of claim 26, wherein the communicating elements are in concentric alignment.

28. The microcannula of claim 25, wherein the communicating elements are in parallel alignment.

29. The microcannula of claim 18, wherein the microcannula comprises two or more reinforcing elements.

30. The microcannula of claim 18, wherein the reinforcing element comprises a coil.

31. The microcannula of claim 18, wherein the reinforcing element is tapered toward the distal end of the microcannula.

32. The microcannula of claim 18, wherein the communicating elements includes a segment chosen from the group consisting of a segment of tubing, a segment of optical fiber and a segment of an electrical conductor.

33. The microcannula of claim 18, wherein the microcannula is configured to fit within a tissue space selected from the group consisting of Schlemm's Canal, an aqueous collector channel, an aqueous vein, a suprachoroidal space and a retinal blood vessel of the eye.

34. The microcannula of claim 18, wherein the distal end has a rounded distal tip.

35. The microcannula of claim 18, wherein the tubular communicating element and the reinforcing element are joined by an outer sheath.

36. The microcannula of claim 35, wherein the outer sheath comprises heat shrink tubing.

37. The microcannula of claim 18, wherein the tubular communicating element and the reinforcing element are joined with an adhesive.

38. The microcannula of claim 18, additionally comprising a lubricious outer coating.

39. The microcannula of claim 17, wherein the second communicating element comprises an optical fiber and the signal beacon delivers visible light.

40. The microcannula of claim 17, wherein the composite microcannula has a flexural rigidity in the range of 3.09 E−11 to 2.86 E−10 kN*m² on a distal portion of the composite microcannula positioned adjacent to the distal end.

41. The microcannula of claim 17, wherein the rounded distal tip acts to disperse light from the signal beacon for improved off-axis visualization.

* * * * *